United States Patent [19]

Georgiev et al.

[11] 4,124,583
[45] Nov. 7, 1978

[54] 5-SUBSTITUTED DERIVATIVES OF 5H-DIBENZ (b,f)-AZEPINE AND METHOD FOR OBTAINING THE SAME

[75] Inventors: Atanas G. Georgiev; Hristo P. Daskalov, both of Sofia, Bulgaria

[73] Assignee: DSO "Pharmachim", Sofia, Bulgaria

[21] Appl. No.: 715,792

[22] Filed: Aug. 19, 1976

[30] Foreign Application Priority Data

Aug. 20, 1975 [BG] Bulgaria .................................. 30823

[51] Int. Cl.$^2$ .......................................... C07D 223/22
[52] U.S. Cl. ................................ 260/239 D; 424/244
[58] Field of Search ..................................... 260/239 D

[56] References Cited

PUBLICATIONS

Douglass et al., "J.A.C.S.", vol. 56, p. 719 (1934).
Smith, The Chemistry of Open-Chain Organic Nitrogen Compounds, vol. I, p. 277, Benjamin Co., N.Y. (1965).

Primary Examiner—Donald G. Daus
Assistant Examiner—D. B. Springer
Attorney, Agent, or Firm—E. Janet Berry; Lawrence Rosen

[57] ABSTRACT

The invention covers the following compounds: 5-(N-benzoylthiocarbamoyl)-5H-dibenz [b, f] azepine, 5-thiocarbamoyl-5H-dibenz [b,f] azepine, 5-(S-methylisothiocarbamoyl)-5H-dibenz [b,f]-azepine and their 10,11-dihydro analogs. These compounds are intermediates for psychoactive drugs.

5 Claims, No Drawings

5-SUBSTITUTED DERIVATIVES OF 5H-DIBENZ (b,f)-AZEPINE AND METHOD FOR OBTAINING THE SAME

This invention refers to 5-substituted derivatives of 5H-dibenz(b,f)-azepine and their salts, which are intermediate products for psychoactive drugs.

There are a number of psychoactive substances derivatives of 5H-dibenz(b,f)-azepine, also known as Iminostilbene, as well as 10,11-dihydro-5H-dibenz(b,f)-azepine, known as Iminodibenzyl, with a general formula I;

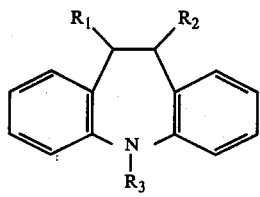

where
$R_1$ and $R_2$ designate a hydrogen or carbon-carbon bond, while $R_3$ (substuent in position 5, respectively), is a basic substituted hydrocarbon residue. For example: the drug Imipramin ($R_1$ and $R_2$ = H, $R_3$ = —$CH_2CH_2CH_2N(CH_3)_2$), described in the Swiss Patent 296 925, and the known drug Opipramol hydrochloride ($R_1$ and $R_2$, carbon-carbon bond,

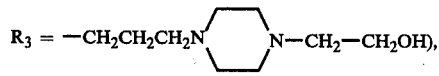

obtained under the German Federal Republic Pat. No. 1 132 556, are also currently used. Compounds with a general formula I also have psychactive properties where $R_1$ and $R_2$ have the abovementioned values, while $R_3$ is a substituted (non-substituted) carbamoyl residue. This group includes substances with pronounced anticonvulsive action, known in therapy as Carbamazepin (U.S. Pat. No. 2,948,718) and Ciheptamide (U.S. Pat. No. 2,762,796).

This invention develops a method of producing 5-substituted derivatives of 5H-dibenz(b,f)-azepine where the substituent should be a residue of thiocarbamic acid, i.e.

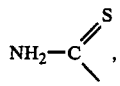

and also suitable N- and S-substituted derivatives of the abovesaid thiocarbamoyl residue.

According to the invention the compounds may be presented by the general formula II

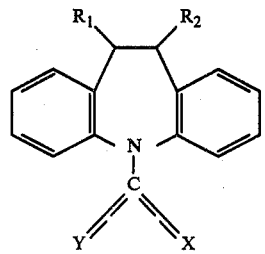

where $R_1$ and $R_2$ designate hydrogen or carbon-carbon bond, X indicates =S or —$SCH_3$, and Y means —$NH_2$; —$NHCOC_6H_5$; =$N^{\oplus}H_2I^{\ominus}$ or =NH. The symbol of a double straight and dotted line ($\equiv\!\equiv\!\equiv\!\equiv$) pictures a simple or double bond between C — X and C — Y, respectively. It is clear that when the bond between the exocyclic carbon atom and the X substituent is double, the bond between this same carbon atom and the Y substituent is simple, and vice versa. According to the invention, compounds with a general formula II and their salts are produced by the respective treatment of mixed anhydride of benzoic and isothiocyanic acid (benzoylisothiocyanate) giving very good results.

According to the method of this invention, Iminostilbene and Iminodibenzyl react readily with benzoylisothiocyanate under soft conditions, producing very high yields of 5-substituted derivatives of 5H-dibenz(b,f)-azepine with a general formula II, where X designate =S and Y —$NHCOC_6H_5$. The easy and high yield of the said compounds is unexpected, considering the difficulties of N-alkylation of 5H-dibenz(b,f)-azepine derivatives (Medicinskaja promishlenost USSR, 1961, No. 12, 10 and the German Pat. No. 1 132 556).

The benzoylthiocarbamoyl compounds obtained, have very high purity and may be used without purification to produce thiocarbamoyl derivatives by hydrolysis in an alkaline medium.

It has been established that this complex process depends on the centration of the alkaline base used. Excess of the fixed concentration disturbs the process of hydrolysis completely: the desired thiocarbamoyl compounds are not obtained, and initial heterocycles are produced instead. In lower than necessary concentrations the process is interrupted altogether, so that the limits within which a preferable concentration of the alkaline base should vary, are very narrow for optimal hydrolysis. On observing the necessary conditions, the process of hydrolysis runs very smoothly and the desired thiocarbamoyl compounds with a general formula II, where X means =S and Y —$NH_2$, are produced in a high (almost quantitative) yield.

The thiocarbamoyl derivatives can be subjected to S-methylation with methyl iodide, resulting in a quantitative yield of isothiurhonium salts with a general formula II, where X indicates —$SCH_3$ and Y — =$N^{\oplus}H_2I^{\ominus}$. For an optimal conduction of the process of S-methylation, it is important to select a suitable solvent. It is preferable to use such organic solvents as ketones (acetone) and aromatic hydrocarbons (benzene, xylene), esters of the lower fatty acids or mixtures of the said solvents.

Isothiurhonium salts interact with strong inorganic bases like sodium and potassium hydroxide or weaker inorganic or organic bases, such as sodium bicarbonate, ammonia, pyridine, etc., producing compounds with a general formula II, where X indicates —SCH$_3$ and Y—=NH.

According to this invention the abovesaid compounds are valuable intermediate products for drug synthesis. N-benzoylthiocarbamoyl derivatives are used to produce thiocarbamoyl compounds which, on their part, are a base for the production of isothiurhonium salts and bases. Compounds with useful anticonvulsive action (Carbamazepin Ciheptamide) are produced from the latter by alkaline hydrolysis.

The following examples explain the invention:

EXAMPLE 1

5-(N-benzoylthiocarbamoyl)-5H-dibenz(b,f)-azepine 5.12 g (0.0642 mole) of ammonium thiocyanate is dissolved in 24 ml of acetone at room temperature, then 6.72 g (0.0464 mole) of benzoylchloride is added quickly to the clear acetone solution. Ammonium chloride precipitate is formed at once. The suspension should be stirred for 1 hour more at room temperature and then a solution of 7.72 g (0.04 mole) 5H-dihenz(b,f)-azepine in 154 ml acetone should be added to it for 30 minutes. After the addition of 5H-dibenz(b,f)-azepine is completed the stirred suspension is heated at reflux for 4 hours. After termination of the abovesaid reaction time 104 ml of acetone is distilled and the precipitate is filtered and washed consecutively in 30 ml of acetone and 84 ml cold water. After drying 10.6–10.7 g of 5-(N-benzoylthiocarbamoyl)-5H-dibenz(b,f)-azepine is produced (m.p. 160–162° C., decomp.). After recrystallization from a mixture of ethylacetate/acetic acid a product with a m.p. 164.5–165° C., decomp., is obtained.

Elemental analysis:

Calculated: for $C_{22}H_{16}N_2OS$ (356.44).

C—74.13%; H—4.52%; N—7.86%; S—9.00%

Found: C—74.30%; H—4.68%; N—7.85%; S—8.81%;

IR: Nujol mull $\nu^{(NH)} = 3400$ cm$^{-1}$; $\nu^{(CO)} = 1730$ cm$^{-1}$.

EXAMPLE 2

5-(N-benzoylthiocarbamoyl)-10,11-dihydro-5H-dibenz(b,f)-azepine 5.12 g (0.0642 mole) of ammonium thiocyanate is dissolved in 24 ml of acetone at room temperature, then 6.72 g (0.0464 mole) of benzoylchloride is added quickly to the clear acetone solution. Ammonium chloride precipitate is separated immediately. The suspension is stirred for 1 hour more at room temperature, then solution of 7.8 g (0.04 mole) Iminodibenzyl in 154 ml acetone is added dropwise for 30 minutes. After the Iminodibenzyl addition is completed, the stirred suspension is reflux for four hours. After that the precipitate of ammonium chloride is filtered, washed with acetone and the combined acetone filtrates distilled to remove acetone. 60 ml of ethylacetate is added to the residual oil and after cooling to 5° C. the crystallized product is filtered and washed with ethylacetate to obtain a colourless filtrate. 6 g of 5-(N-benzoylthiocarbamoyl)-iminodibenzyl is obtained (m.p. 151°–152° C., decomp.).

Elemental analysis:

Calculated: for $C_{22}H_{18}N_2OS$ (358.46).

C—73.72%; H—5.06%; N—7.86%; S—8.94%;

Found: —C—74.50%; H—4.90%; N—7.80%; S—8.67%;

IR: Nujol mull —$\nu^{(NH)}$— = 3160 cm$^{-1}$; $\nu^{(CO)} = 1715$ cm$^{-1}$.

EXAMPLE 3

5-(thiocarbamoyl-5H-dibenz(b,f)-azepine 3.56 g (0.01mole) of 5-(N-benzoyl thiocarbamoyl)-5H-dibenz(b,f)-azepine is suspended into 37.5 ml of cold water. 3.6 ml of 30% aqueous potassium hydroxide is added and the suspension is heated to boilling. A yellow solution is produced, out of which the reaction product (5-thiocatbamoyliminostilbene) starts to separate after 15 minutes. After boiling for 2.5 hours the suspension is cooled to 25° C. and the desired product is separated by filtration, washed profusely with cold water (25° C.), until the pH of rinsing water is adjusted to about 5. After drying at 50° C., 2.38 g of 5-thiocarbamoyl-5H-dibenz(b,f)-azepine is obtained (m.p. 192°–194° C.). After recrystallization from benzene a product with a 197°–197.5° C. melting point is obtained.

Elemental analysis:

Calculated: for $C_{15}H_{12}N_2S$ (252.34).

C—71.39%; H—4.79; N—11.10%; S—12.71%;

Found: —C—71.00%; H—5.10%; N—11.00%; S—12.47%;

EXAMPLE 4

5-(thiocarbamoyl)-10.11-dihydro-5H-dibenz(b,f)-azepine 3.58 g (0.01 mole) of 5-(N-benzoylthiocarbamoyl)-iminodibenzyl is suspended into 37.5 ml of cold water and 3.6 ml of 30% aqueous potassium hydroxide is added. The suspension heated to boiling point. A colourless solution is produced, out of which the reaction product (5-thiocarbamoyl-iminobenzyl) starts to separate after 15 minutes. After boiling for 2.5 hours, the suspension in cooled to 25° C. and the desired product is separated by filtration washed profusely with cold water (25° C.), until the pH of the rinsing water is adjusted to about 5. After drying at 50° C., 2.4 of 5-thiocarbamoyliminodibenzyl is produced. (m.p. 207°–209° C.). After recrystallization from xylene a product with a m.p. 213.5°–215° is obtained.

Elemental analysis:

Calculated: for $C_{15}H_{14}N_2S$ (254.36).

C—70.83%; H—5.55%; N—11.01%; S—12.61%;

Found: —C—71.50%; H—5.00%; N—11.20%; S—12.37%

EXAMPLE 5

5-(S-methylisothiocarbamoyl)-5H-dibenz(b,f)-azepine hydroiodide.

2.52 g (0.01 mole) of 5-(thiocarbamoyl)-5H-dibenz(b,f)-azepine is dissolved by boiling in 50 ml of acetone. Then the clear acetone solution is cooled to 25° C. and 1.71 g (0.012 mole) of methyliodide is added and the solution is heated to its boiling point. 5 minuted after the boiling has started the reaction product 5-(S-methylisothiocarbamoyl)-5H-dibenz(b,f)-azepine hydroiodide begins to separate. The boiling of acetone continues for 4 hours and then the desired product is separated by filtration. The precipitate is washed with 15 ml of acetone and dried at 50° C. 3.60 g of 5-(S-methylisothiocarbamoyl)-5H-dibenz(b,f)-azepine hydroiodide (m.p. 187°–191° C.) is obtained. After recrystallization from water a product with a melting point 189°–192° C. is produced.

Elemental analysis:

Calculated: for $C_{16}H_{15}IN_2S$ (394.28).

C—48.74%; H—3.84%; N—7.11%; I—32.18%;

Found: —C—49.00%; H—4.10%; N—7.30%; I—31.00%.

EXAMPLE 6

5-(S-methylisothiocarbamoyl)-10,11 - dihydro-5H-dibenz(b,f)-azepine hydroiodide.

2.54 g (0.01 mole) of 5-(thiocarbamoyl)-iminodibenzyl is dissolved by boiling in 240 ml benzene. After cooling the solution to 30° C., 1.171 g (0.012 mole) of methyliodide is added and the solution is heated at reflux for 4 hours. The reaction product 5-(S-methylisothiocarbamoyl)-iminodibenzyl hydroiodide is separated by filtration, washed with 10 ml of benzene and dried at 50° C.

3.4 g of 5-(S-methylisothiocarbamoyl)-iminodibenzyl hydroiodide are produced (m.p. 183°-185° C., decomp.). After recrystallization from water a product with a melting point 184° C., decomp. is produced.

Elemental analysis:
Calculated: for $C_{16}H_{17}IN_2S$ (396.29).
C—48.49%; H—4.32%; N—7.07%; I—32.02%;
Found: —C—49.00%; H—4.10%; N—6.94%; I—31.06%;

EXAMPLE 7

5-(S-methylisothiocarbamoyl)-5H-dibenz(b,f)-azepine 10 g (0.0254 mole) of 5-(S-methylisothiocarbamoyl)-5H-dibenz(b,f)-azepine hydroiodide is dissolved in 100 ml of methanol at room temperature. 15 ml of 8% aqueous sodium hydroxide is added dropwise to the clear methanol solution; the homogenous solution is stirred for 15 minutes and then 200 ml of water is added. After two hours the precipitate is separated and washed with water at pH 5. The yield of 5-(S-methylisothiocarbamoyl)-5H-dibenz(b,f)-azepine is 5.8 g (m.p. 118°-120° C.). The melting point of the product recrystallized from cyclohexane, is 123°-125° C.

Elemental analysis:
Calculated: for $C_{16}H_{14}N_2S$ (266.37).
C—72.14%; H—5.30%; N—10.52%; S—12.03%;
Found: C—75.10%; H—5.80%; N—10.80%; S—12.37%.

IR: Nujol mull —$\nu^{(NH)} = 3340$ cm$^{-1}$.

EXAMPLE 8

5-(S-methylisothiocarbamoyl)-10,11-dihydro-5H-dibenz(b,f)-azepine 10 g (0.0252 mole) of 5-(S-methylisothiocarbamoyl)-10.11-dihydro-5H-dibenz(b,f)-azepine hydroiodide is dissolved in 100 ml of methanol at room temperature. 15 ml of 8% aqueous sodium hydroxide is added to the clear methanol solution and the solution is stirred for 15 minutes at room temperature. Then 200 ml of water are added and after stirring for 30 minutes, the precipitate separated is filtered and washed with water to pH 5.

The yield of 5-(S-methylisothiocarbamoyl)-10.11-dihydro-5H-dibenz(b,f)-azepine is 6.0 g (m.p. 96°-&7° C.). The melting point of the product recrystallized from cyclohexane is 100°-101° C.

Elemental analysis:
Calculated: for $C_{16}H_{16}N_2S$ (268.38).
C—71.61%; H—6.01%; N—10.52%; S—11.95%
Found: C—71.80%; H—5.50%; N—10.80%; S—11.65%.

IR: Nujol mull $\nu^{(NH)} = 3290$ cm$^{-1}$.

We claim:

1. Compounds having the formula (III):

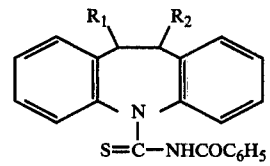

wherein $R_1$ and $R_2$ represent substituents selected from the group consisting of hydrogen bonds or carbon to carbon bonds in the 10th and 11th positions of the dibenz(b,f)-azepine.

2. Compounds having the formula (IV):

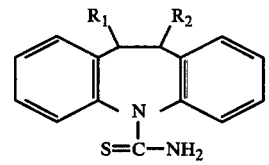

wherein $R_1$ and $R_2$ represent substituents selected from the group consisting of hydrogen bonds or carbon to carbon bonds in the 10th and 11th positions of the dibenz(b,f)-azepine.

3. Compounds having the formula (V):

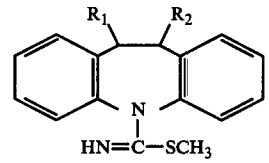

and their salts formed with hydroiodic acid wherein $R_1$ and $R_2$ represent substituents selected from the group consisting of hydrogen bonds or carbon to carbon bonds in the 10th and 11th positions of the dibenz(b,f)-azepine.

4. 5-(N-benzoylthiocarbamoyl)-5H-dibenz(b,f)-azepine.

5. 5-(N-thiocarbamoyl)-5-H-dibenz(b,f)-azepine.

* * * * *